United States Patent
Arbuckle et al.

(10) Patent No.: US 6,881,539 B1
(45) Date of Patent: Apr. 19, 2005

(54) TRANSPOSABLE ELEMENT-ANCHORED, AMPLIFICATION METHOD FOR ISOLATION AND IDENTIFICATION OF TAGGED GENES

(75) Inventors: John A. Arbuckle, Woodbury, MN (US); Timothy W. Fox, Des Moines, IA (US); Robert B. Meeley, Des Moines, IA (US); Benjamin A. Bowen, Berkeley, CA (US); John A. McElver, Durham, NC (US)

(73) Assignee: Pioneer Hi-Bred International Inc., Des Moines, IA (US)

( * ) Notice: Subject to any disclaimer, the term of this patent is extended or adjusted under 35 U.S.C. 154(b) by 0 days.

(21) Appl. No.: 09/622,353

(22) PCT Filed: Feb. 16, 1999

(86) PCT No.: PCT/US99/03196

§ 371 (c)(1),
(2), (4) Date: Sep. 12, 2000

(87) PCT Pub. No.: WO99/41415

PCT Pub. Date: Aug. 19, 1999

Related U.S. Application Data

(60) Provisional application No. 60/074,931, filed on Feb. 17, 1998.

(51) Int. Cl.[7] .............................. C12Q 1/68; C12P 19/34
(52) U.S. Cl. .............................. 435/6; 435/91.2; 935/77
(58) Field of Search ....................... 435/6, 91.2; 935/77

(56) References Cited

U.S. PATENT DOCUMENTS

| | | | |
|---|---|---|---|
| 5,684,242 A | * | 11/1997 | Schnable et al. ........... 800/205 |
| 5,707,809 A | * | 1/1998 | Halverson et al. ............. 435/6 |
| 5,710,367 A | * | 1/1998 | Kindiger et al. ............ 800/200 |
| 5,958,738 A | * | 9/1999 | Lindemann et al. ....... 435/91.2 |
| 5,962,764 A | * | 10/1999 | Briggs et al. ............... 800/270 |

OTHER PUBLICATIONS

Walbot et al., Regulation of Mu element copy number in maize lines with an active or inactive Mutator transposable element system, 1988, Mol. Gen. Genet., vol. 211, p. 27–34.*

Grunder et al., Polymorphisms in the carboxy–terminus of the epithelial sodium channel in fat models for hypertension, J. of hypertension, 1997, vol. 15(2), p. 173–179.*

Straus et al. Genomic subtraction for cloning DNA corresponding to deletion mutations, Proc. Natl. Acad. Sci. USA, 1990, vol. 87, p. 1889–1893.*

* cited by examiner

*Primary Examiner*—Kenneth R. Horlick
*Assistant Examiner*—Joyce Tung
(74) *Attorney, Agent, or Firm*—Steve Callistein

(57) ABSTRACT

A method for the rapid isolation and identification of the DNA sequence of transposable element-tagged genes is provided. The method comprises a modified AFLP approach using a transposable element-anchored amplification to identify and clone an amplification product that is associated with a mutant phenotype. Once cloned, the amplification product of interest may be used to screen a cDNA library directly or may be sequenced and compared to available databases for sequence homology. A modification of this approach provides a method for the identification of the location of an additional type of insertion event into genomic DNA, more specifically transgene insertion into the genome of a host organism.

21 Claims, No Drawings

TRANSPOSABLE ELEMENT-ANCHORED, AMPLIFICATION METHOD FOR ISOLATION AND IDENTIFICATION OF TAGGED GENES

This application claims the benefit of Provisional Application No. 60/074,931, filed Feb. 17, 1998.

FIELD OF THE INVENTION

The present invention relates to the field of genetics, more specifically to molecular biology and methods for gene isolation and identification.

BACKGROUND OF THE INVENTION

Manipulation of transposable element families within, or derived from, the maize genome is a proven technique for the isolation of plant genes (see Chandler (1994) in *The Maize Handbook*, ed. Freeling and Walbot (Springer-Verlag, New York), pp. 647–652). The maize transposable element family, Mutator, has one of the highest forward mutation rates known in nature; these elements exhibit a high frequency of germinal insertion, an apparent bias for insertion into transcribed regions, and frequent, late, somatic excision. Mutator is represented by six classes of member elements whose DNA sequences are known, and so-called active Mutator lines depend upon the presence and expression of the autonomous regulatory element Mu-DR (Robertson (1978) *Mutation Res.* 51:21–28; Chandler and Hardeman (1992) in *Adv. Genet.*, 30:77–122). The sequence conservation of the 220 base pair terminal-inverted-repeat DNA (TIR) of these elements has been exploited for PCR-based selection and functional analysis of insertion mutants for known DNA sequences, as embodied by the Trait Utility System for Corn (TUSC) program. While TUSC is designed for reverse genetics, a similar scheme assists cloning transposon-tagged genes in forward genetics fashion.

Forward gene tagging with Mutator is initiated by creating genetic crosses between donor Mu-active and recipient inactive lines. Mu-donor lines contain the Mu-DR regulatory element (Chomet et al. (1991) *Genetics* 122:447457) and high copy number of Mu elements, whereas the recipient lines are inbred lines having no active Mu elements. The Mu-donor line is usually chosen as the male parent because a greater number of mutagenized gametes can be sampled through the pollen. Those germinal insertion events that disrupt gene function predominantly behave as recessive mutations, so mutant phenotypes are most often discovered by observing the F2 progeny of the donor x recipient cross.

Once a phenotype of interest is noted, cosegregation analysis is performed within the mutant family. DNA is isolated from mutant individuals and subjected to restriction enzyme digestion and Southern analysis. Radiolabeled probes for each Mu element class are hybridized in-succession to the Southern blot to search for Mu-containing restriction fragments that cosegregate with the phenotype in question. A subgenomic library is then prepared by excising the cosegregating fragment from an agarose gel and cloning into a suitable vector. Positive clones must be identified with the appropriate Mu probe; each candidate must then be characterized by restriction mapping, subcloning, sequence analysis, and confirmation. Amplified Fragment Length Polymorphisms (AFLP) technology has been designed to generate large numbers of randomly distributed molecular markers (see, for example, European Patent Application No. 0534858 A1).

Despite the elegant genetic and molecular methods involved in transposon tagging, the field and laboratory processes involved are frequently protracted and very labor intensive. A more efficient method for rapid isolation and identification of transposable element-tagged genes is needed. The present invention provides this and other advantages.

SUMMARY OF THE INVENTION

The present invention provides for fewer laboratory manipulations and provides for the immediate molecular analysis of a transposable element-tagged genetic sequence of interest by allowing for direct isolation of DNA fragments comprising a portion of the tagged genetic sequence. The present method mitigates much of the laborious outcrossing, Southern analysis, library construction, and subcloning presently associated with isolation and identification of transposable element-tagged genes that cause a detectable mutant phenotype.

In one object, the present invention provides for a method for the identification and isolation of a genetic sequence from an organism, wherein disruption of genomic DNA of said organism by a transposable element flanking the genetic sequence is associated with a mutant phenotype. The method comprises the steps of segregating a plurality of organisms by the presence or absence of the mutant phenotype. The genomic DNA of each organism comprises at least one copy of said transposable element. A mutant genomic DNA sample is obtained from at least one of the organisms exhibiting said mutant phenotype and a wild-type genomic DNA sample is obtained from at least one of said organisms not exhibiting said mutant phenotype. At least one of the mutant and at least one of the wild-type genomic DNA samples are fragmented to produce DNA fragments. An adapter is attached to at least one of the mutant DNA fragments and to at least one of the wild-type DNA fragments, resulting in a collection of adapter-modified DNA fragments. The mutant and wild-type adapter-modified DNA fragments are amplified to yield an amplification product comprising the genetic sequence flanked by: 1) a transposable element derived sequence and, 2) an adapter derived sequence. In the method, the amplification employs at least two oligonucleotide primers, with one of the primer sequences selectively hybridizing, under stringent hybridization conditions, to the adapter sequence and the other primer selectively hybridizing, under stringent hybridization conditions, to the transposable element. An amplification product derived from the organism exhibiting the mutant phenotype and absent in the organism not exhibiting the mutant phenotype is isolated. The isolated amplification product comprises the genetic sequence associated with the mutant phenotype.

In optional embodiments, cosegregation analysis or bulk segregant analysis can be performed to identify an amplification product associated with the mutant phenotype. In certain embodiments amplification is performed by the polymerase chain reaction (PCR). The transposable element Mutator is used in preferred embodiments.

In an additional object, the present invention also provides for the identification of transgenic insertions into genomic DNA of a host organism. The transgene-derived sequence can be sequenced and/or used to probe mapping populations to determine the genomic location of each transgene insertion event.

Definitions

Units, prefixes, and symbols may be denoted in their SI accepted form. Numeric ranges are inclusive of the numbers defining the range and include each integer within the defined range. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

As used herein, "heterologous" in reference to a nucleic acid is a nucleic acid that originates from a foreign species, or, if from the same species, is substantially modified from its native form in composition and/or genomic locus by human intervention.

As used herein, the term "genetic sequence" refers to a nucleic acid sequence from a genome of an organism whereby insertion of a transposable element directly adjacent to that nucleic acid disrupts gene function resulting in a mutant phenotype. The gene or regulatory region of which the genetic sequence is a part of is said to be "tagged" by the transposable element. The genetic sequence can be a sequence derived from a gene (e.g., exon, intron, 5' or 3' untranslated regions (UTR)), or from a gene regulatory region such as a promoter or enhancer.

As used herein, the term "organism" includes reference to whole organisms, or organs, tissues, or cells thereof.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of human intervention. The term "recombinant" as used herein does not encompass the alteration of the cell or vector by naturally occurring events (e.g., spontaneous mutation natural transformation/transduction/transposition) such as those occurring without human intervention.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 100 nucleotides in length, optionally no more than 50, or 25 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about is 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 138:267–284 (1984): $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part 1, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

As used herein, "transgene" refers to a heterologous nucleic acid that is introduced into a host genome by human intervention. The transgene can be artificial in origin, originate from a non-host species, or if from the same species its sequence is modified, by human intervention, in vivo or in vitro. The transgene, or an expression cassette which comprises the transgene, can be differentiated from host nucleic acids by a nucleic acid probe/primer which selectively hybridizes to the transgene under stringent hybridization conditions.

"Transgenic" is used herein to include any eukaryotic or prokaryotic genome, cell, cell line, tissue, or organism, the genotype of which has been altered by the presence of heterologous nucleic acid including those transgenics initially so altered as well as those created by sexual crosses or asexual propagation from the initial transgenic.

As used herein, "transgenic plant" includes reference to a plant which comprises within its genome a heterologous nucleic acid. Generally, the heterologous nucleic acid is stably integrated within the genome such that the heterlogous nucleic acid is passed on to successive generations. The heterologous nucleic acid may be integrated into the genome alone or as part of an expression cassette. The term "transgenic plant" as used herein does not encompass the alteration of the genome (chromosomal or extra-chromosomal) by conventional plant breeding methods or by naturally occurring events such as random cross fertilization, non-recombinant viral infection, non-recombinant bacterial transformation, non-recombinant transposition, or spontaneous mutation.

The term "transposable element" as used herein includes reference to a nucleic acid sequence that can move (transpose) from one locus to another in a cell. Transposition can be replicative wherein one copy of the transposable element remains at the donor site and another is inserted at the target site; or transposition can occur conservatively wherein the transposable element is excised from one site and inserted at the other. The term includes, but is not limited to, transposable elements found in prokaryotes such as insertion sequences (IS), transposons (Tn), or bacteriophages such as Mu and D108. Eukaryotic transposable elements include, but are not limited to: Copia elements as are found in *D. melanogaster*; TY elements such as those found in yeast; Ta1 and Tnt 1 transposable elements such as those found in *Arabidopsis*; IAP found in mice; Tam or Cin transposable elements such as those found in snapdragon; and AC, Spm, Bs, Cin, Dt, and Mutator transposable elements such as those found in maize. The term is also inclusive of synthetic transposable elements which can insert themselves either replicatively or conservatively within a host genome and whose transposition or excision from the genome can be controlled by human intervention. For example, a synthetic transposable element can be constructed which lacks a functional transposase (the enzyme that mediates transposition) but which is supplied in trans by operably linking the transposase gene to an inducible promoter.

DETAILED DESCRIPTION OF THE INVENTION

Overview and Utility

The method of the present invention provides for the isolation and/or identification of a genetic sequence from a gene (or its regulatory control region) which has been disrupted by insertion of a transposable element. Insertion of the transposable element directly adjacent to the genetic sequence in the host organism's genome results in altered gene expression which is associated with a mutant phenotype in that organism.

The genetic sequence can be used as a probe or amplification primer in the detection, quantitation, or isolation of gene transcripts or of a gene regulatory region. For example, the isolated genetic sequence can be used as a probe in detecting deficiencies in the level of mRNA in screenings for desired transgenic plants, for detecting mutations in the gene (e.g., substitutions, deletions, or additions), for monitoring upregulation of expression, for detection of any number of allelic variants (polymorphisms), orthologs, or paralogs of the gene (particularly for the Gramineae), or for site directed mutagenesis in eukaryotic cells (see, e.g., U.S. Pat. No. 5,565,350).

The genetic sequence can also be employed for use in sense or antisense suppression of one or more genes in a host cell, tissue, or plant. Attachment of chemical agents which bind, intercalate, cleave and/or crosslink to the genetic sequence can also be used to modulate (inhibit or increase) gene transcription or translation.

A genetic sequence of the present invention can also be used for recombinant expression of its encoded polypeptide, or for use as immunogens in the preparation and/or screening of antibodies. Such antibodies can be used in assays for expression levels, for identifying and/or isolating homologous genes from expression libraries, for identification of homologous polypeptides from other species, or for purification of the polypeptide encoded by genes identified by the methods of the present invention.

Segregation of Organisms

In accordance with the method of the present invention, individual organisms whose genomic DNA comprises at least one transposable element-tagged gene are segregated by the presence or absence of a mutant phenotype of interest. The mutant phenotype of the organism should be one known or suspected of arising from disruption of a single gene by insertion of a transposable element or, at the least, such an insertion event cannot be ruled out. Those of skill in the art will understand that the pool of organisms to be segregated should be grown or cultured under similar conditions to avoid segregation of phenotypes arising from non-genetic contributions (e.g., environmental effects).

The method of the present invention can be applied to any phenotype which can be distinguished and classified as either wild-type or mutant. Such phenotypes can be detectable by visual, biochemical, agronomic, or morphological means. Those of skill will recognize that the terms "wild-type" and "mutant" as used herein are arbitrary terms used to differentiate organisms according to the presence or absence of a particular phenotype.

The organisms to which the present invention can be applied can be prokaryotic or eukaryotic. Eukaryotic organisms can be haploid or diploid when employed in the methods of the present invention. In diploid organisms exhibiting the wildtype phenotype may be from the F1 generation, but mutant phenotypes associated with transposon-tagged genes more commonly show up as recessive mutants, and hence more commonly appear in the F2 generation. Thus, in a preferred embodiment of the invention, the organisms will be from the F2 generation of a cross between a transposable element-donor individual and a recipient inbred individual having no active transposable elements. Preferably, the methods of the present invention will be applied to plants. A particularly preferred plant is a monocot such as those of the family Gramineae, including such exemplary species as *Zea mays*. In a particularly preferred embodiment of the invention, the organisms having transposable elements will be maize plants from the F2 generation of a cross between a Mu-donor individual containing the Mu-DR regulatory element (Chomet et al. (1991) *Genetics* 122:447457) and high copy number of Mu elements and a recipient inbred individual having no active Mu elements.

The genomic DNA of the organisms will have at least one transposable element, and preferably a plurality of transposable elements such as at least 5, 10, 25, 50, or 100.

Transposable elements within the genome can be of the same or differing types. Organisms comprising transposable elements can be experimentally derived according to methods available in the art. See, for example, Chomet (1994) in *The Maize Handbook*, ed. Freeling and Walbot (Springer-Verlag, New York), pp. 243–248. In a preferred embodiment, the transposable element is Mutator (Mu). Robertson (1978) *Mutation Res.* 51:21–28, Chandler and Hardeman (1992) *Advances in Genetics* 30:77–122). The terminal-inverted-repeat DNA (TIR) present in many transposable elements, including Mu, is well suited to the present invention.

Insertion of a transposable element may occur within or near a transposable element-tagged gene's DNA sequence. The transposable element-tagged gene to be identified with the method of the present invention may have a transposable element inserted within the gene's coding sequence, such that transcription of the gene's normal functional product is disrupted, leading to a mutant phenotype. Alternatively, the tagged gene may have a transposable element inserted within an intron, such that RNA splicing is affected, which in turn may disrupt the functional gene product, thereby yielding a mutant phenotype. Further, the tagged gene can have a transposable element inserted within a gene control region such as a promoter or enhancer element such that gene expression is increased or decreased leading to a mutant phenotype.

For each phenotype to which the method of the present invention is applied, at least one organism having a wild-type phenotype and at least one mutant are segregated. Optionally, at least 2, 4, 5, 10, 15, or 20 organisms are present in the segregated wild-type population and at least 2, 4, 5, 10, 15, or 20 are present in the segregated mutant population. The number of organisms in each class is dependent upon the desired probability of finding a recessive, optionally at least 50%, 75%, 80%, 90%, or 99%. See, Genetic Experiments and Mapping, E. H. Coe, The Maize Handbook—M. Freeling, V. Walbot, eds. Pp. 189–197, 1994.

Obtaining Genomic DNA from the Organism

In the method of the present invention, genomic DNA samples are obtained from at least of the organisms exhibiting the mutant phenotype and from one of the organisms not exhibiting the mutant phenotype (i.e., a wild-type organism). Methods for obtaining genomic DNA from a wide range of prokaryotes and eukaryotes is well known to those of ordinary skill in the art. See, e.g., Exemplary genomic DNA isolation protocols are described in *Plant Molecular Biology: A Laboratory Manual*, Clark, Ed., Springer-Verlag, Berlin (1997); *Current Protocols in Molecular Biology*, Ausubel, et al., Eds., Greene Publishing and Wiley-Interscience, New York (1995); Taylor et al. (1993) in *Methods in Plant Molecular Biology and Biotechnology*, ed. Glick et al. (CRC Press, Boca Raton, Fla.), pp. 3841. Additionally, genomic DNA isolation kits are commercially available from a number of vendors such as Invitrogen (Carlsbad, Calif.). Further, genomic DNA isolation services are provided by such companies as Stratagene (La Jolla, Calif.).

In preferred embodiments, genomic DNA is obtained from plants. Generally, plant cell walls are broken or digested to allow access to intracellular constituents and cell membranes are disrupted to release the DNA. Disruption is often achieved by using a detergent such as sodium dodecy sulphate (SDS) or cetyl trimethylammonium bromide (CTAB). Extraction of whole genomic DNA using CTAB has been successfully used with a wide range of monocot and dicot species. The method may be used with either fresh or dehydrated plant material. A CTAB based method of DNA extraction is preferred. See, for example, Saghai Maroof (1984) *Proc. Natl. Acad. Sci. USA* 81:8014–8019. For the purpose of increasing throughput (i.e., screening multiple families segregating for various mutations), a 96-well format of DNA extraction may be employed. An alternate extraction method relies use of hot SDS. Dellaporta et al., *Plant Mol Biol Rep* 1(4):19–21 (1983). For particularly difficult isolations, for example plants high in polyphenolics or polysaccharides, an initial concentration of the nuclei away from most cytoplasmic components can be performed. Henfrey and Slater, Isolation of Plant Nuclei. In: Methods in molecular biology, vol. 4 (1988). Humana Press, Totowa, N.J., pp. 447–452. Those of ordinary skill in the art will recognize that methods to obtain the genomic DNA of a wild-type or mutant organism is not a critical aspect of the present invention and may be achieved by a variety of means which provide for sufficiently intact DNA of adequate yield and purity.

Fragmentation of DNA

After obtaining genomic DNA samples from mutant and wildtype organisms, the genomic samples are fragmented to produce mutant and wild-type DNA fragments. Fragmenting the genomic DNA can be accomplished using, but not limited to, chemical, mechanical, sonic, electromagnetic, radioactive, or enzymatic methods. Preferably, the fragmented DNA is typically in the range of about 100 to 3000 base pairs in length, more preferably about 250 to 1000 base pairs in length. In preferred embodiments, fragmentation is accomplished using restriction enzymes, preferably a four-base cutter, more preferably the restriction enzymes MseI, MspI, Hinp1I, and BfaI. In particularly preferred embodiments, fragmentation is achieved by using a double-restriction digest of isolated DNA (usually with a four-based cutter coupled with a six-base cutter) to form 5' or 3' overhangs. The fragmentation procedure results in mutant and wildtype DNA samples each of which comprises a collection of DNA fragments.

Attachment of Adapters

The mutant and wild-type DNA fragments of the present invention are modified by attachment of an adapter to form mutant and wild-type adapter-modified DNA fragments. The term "adapter" as used herein refers to a nucleic acid sequence that is or can be converted to a blunt ended nucleic acid or a nucleic acid having a 5' or 3' overhang. Adapters can be added as short pre-synthesized oligomers. These oligomeric sequences can be attached to the DNA fragments using, for example, chemical or enzymatic means. Enzymatic attachment is conveniently accomplished using a DNA ligase. Various DNA ligases such as T4 DNA ligase, Pfit DNA ligase, and E. coli DNA ligase are available through commercial vendors.

Depending upon the DNA fragmentation method, the termini of the DNA fragments may need to be rendered compatible with the terminus of the adapter to which they will be attached. For example, single-strand specific nucleases can be used to treat DNA fragments with single strand overhangs to prepare them for attachment of blunt-ended adapters. In preferred embodiments, the DNA fragments comprise at least one overhang restriction site. A double-stranded adapter sequence complementary to the overhang restriction sites on each of these fragments can be attached to at least one of the overhang restriction sites on each DNA fragment.

Adapter sequences can also be added by successive addition of single nucleotides. Methods of polymerizing nucleotides to DNA fragments are known in the art and include use of such enzymes as terminal deoxynucleotidyl transferase. Alternatively, nucleotides forming the adapter sequence can be added to the DNA fragment by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template.

Amplification of Adapter-Modified DNA Fragments

Double-stranded adapters on the adapter-modified wild-type and mutant DNA fragments serve as priming sites for subsequent primer-dependent amplifications using primers derived from each adapter. The amplification products produced comprise a genetic sequence flanked by the transposable element on one end and the adapter sequence on the other end.

The amplification step employs two oligonucleotide primers, with one of the primers being derived from the adapter sequence and the other primer being derived from the sequence for the transposable element. Primers are designed such that they selectively hybridize, under stringent hybridization conditions, to the nucleic acid sequence from which they were derived. Suitable oligonucleotide primer sequences may be designed by methods known in the art, based on the known sequences of the double-stranded adapter and the transposable element that will serve as template DNA during the amplification. See, for example, Rychlik (1993) in *Methods in Molecular Biology: PCR Protocols, Current Methods, and Applications*, ed. White (Humana Press, Totowa, N.J.), vol. 15, pp. 31–40. In one preferred embodiment of the invention, the transposable element comprises a tandem inverted repeat sequence (TIR) that serves as the template for the primer, and more preferably the transposable element is a Mu-transposon. When the transposable element-derived primer is derived from the terminal inverted repeat (TIR) sequence of a transposable element, the possibility exists of detecting two amplification products, as TIR-derived primers can amplify bidirectionally from the transposable element's left and right borders. In this case, the two amplification products represent portions of the gene residing 5' and 3' to the inserted transposable element.

The amplification reaction can be run using protocols well known in the art and experimentally optimized for the oligonucleotide primers of choice. See, for example, Delidow et al. (1993), in *Methods in Molecular Biology: PCR Protocols, Current Methods, and Applications*, ed White (Humana Press, Totowa, N.J.), vol. 15, pp. 129; Sambrook et al. (1989) *Molecular Cloning: A Laboratory Manual* (Cold Spring Harbor Laboratory Press, Plainview, N.Y.), herein incorporated by reference. Preferably, amplification is achieved using the polymerase chain reaction (PCR).

The method of the present invention may comprise a preliminary amplification step following attachment of adapter sequences and before a first amplification step that generates the amplification products. This preliminary amplification step, which also amplifies adapter-modified DNA fragments that comprise DNA flanked by said transposable element and said adapter sequence, employs the same two oligonucleotide primers as used in the first amplification, except that the primer derived from the transposable element whose sequence is inserted into the transposable element-tagged gene is a nonlabeled primer. The amplified products of this preliminary amplification step are then subjected to the first amplification step using the same primer pairs, preferably wherein at least one primer is labeled. Preferably, the preliminary and first amplifications are performed by PCR.

AFLP amplification is optionally a two step affair. The first step comprises amplifying DNA fragments with an adapter-specific primer pair, in which each primer extends one nucleotide into the restriction fragment (base selection is arbitrary). In the second step, the products of the first step are amplified with an adapter-specific primer pair in which each primer has been extended an additional two nucleotides into the restriction fragment (also chosen arbitrarily). Extending the primer sequences into the restriction fragment targeted for amplification achieves an increased level of selectivity during amplification.

In one preferred embodiment of the invention, the preliminary amplification may consist of an AFLP-like approach, wherein the adapter-ligated DNA restriction fragments are subjected to both a preliminary and a secondary PCR amplification. The preliminary PCR amplification uses a high-Tm Mu-derived primer that complements the TIR sequence of a Mu transposable element inserted into the gene of interest. By "Tm" is intended the temperature at which an oligonucleotide primer will anneal to its complementary sequence residing in the template DNA. In any round of PCR amplification, the annealing temperature chosen will determine whether the Tm requirement of a particular oligonucleotide primer is met. Thus, to allow for annealing of a particular primer of interest to its complementary template DNA, the annealing temperature must be within the range of the primer's calculated Tm. In this preferred embodiment of the invention, the preliminary PCR may consist of an AFLP-like approach, wherein the high-Tm Mu-TIR-derived primer during the preliminary PCR amplification is paired with an adapter-derived primer having a similar high Tm. With this approach, DNA restriction fragments that are flanked by adapter sequences will be amplified as well as Mu-containing restriction fragments, as only one annealing temperature is used during the annealing phase of any given denaturation-annealing-polymerization thermocycle.

Alternatively, a TAIL-PCR approach may be taken during the preliminary round of amplification. By "TAIL-PCR" is intended a thermal asymmetric interlaced PCR, wherein the two oligonucleotide primers have different Tm requirements and the denaturation-annealing-polymerization thermocycles are manipulated to preferentially amplify a specific target sequence (see particularly Liu and Whittier (1995) *Genomics* 25(3):674–681 and Liu et al. (1995) *Plait J.* 8(3):457–463). In the case of this embodiment of the invention, a high-Tm Mu-TIR-derived primer is paired with a low-Tm adapter-derived primer. Initial denaturation-annealing-polymerization thermocycles are conducted at an annealing temperature that favors annealing of Mu-TIR-derived primer to its complementary Mu-containing restriction fragments. These Mu-containing sequences are then preferentially and geometrically amplified over nontarget sequences, by interspersion of thermocycles having low annealing temperatures favorable for annealing of the adapter-derived primer with thermocycles having high annealing temperatures favoring annealing of the Mu-TIR-derived primer. Ideally, this strategy will eliminate amplification of most of the DNA restriction fragments that are flanked by adapter sequences, thereby enriching for Mu-containing products.

The amplification products derived from either of these preliminary amplification methods are then diluted and used as template for a second round of amplification. This secondary amplification uses a touchdown of annealing temperatures and is performed with a nested Mu-TIR-derived primer (preferably, radiolabeled or labeled with fluorescent dye) paired with a nested adapter-derived primer. This "touchdown" procedure entails setting the initial high annealing temperature of the PCR thermocycling profile 2° C. higher than the calculated Tm of the Mu-TIR-derived primer. The annealing temperature is then dropped by one-degree intervals over a set number of denaturation-annealing-polymerization thermocycles until a desired low annealing temperature is reached. This low annealing temperature, which is about 5° C., preferably is about 6° C., more preferably is about 7° C. below the initial high annealing temperature, is the annealing temperature used during the annealing phase of the remaining denaturation-annealing-polymerization thermocycles. Thus, for example, if the Tm of the Mu-TIR-derived primer is 62° C., the initial annealing temperature would be 64° C.; and if the final desired annealing temperature is 57° C., the low annealing temperature would be reached within 7 thermocycles. By "nested primer" is intended a primer that has been extended at least one nucleotide into the restriction DNA fragment targeted for amplification. By running 4 reactions, all Mu-flanking sequences of amplifiable size will be propagated.

Detection of Amplification Products

The amplification products are labeled to permit detection. Labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes, radiolabels, enzymes, and calorimetric labels.

In some embodiments, the label is simultaneously incorporated during the amplification step in the preparation of the nucleic acids. Thus, for example, polymerase chain reaction (PCR) with labeled primers or labeled nucleotides will provide a labeled amplification product. Non-radioactive probes are often labeled by indirect means. For example, a ligand molecule is covalently bound to the primer. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody. Preferably the amplification products are electrophoresed through an acrylamide sequencing gel to achieve separation. The gel is then dried and autoradiography or phosphor-screen exposure is performed to detect radiolabeled or fluorescence-labeled bands, respectively.

Analysis of Amplification Products

Any number of methods can be employed to identify and isolate the amplification product which is statistically associated with the mutant phenotype in the organism. In cosegregation analysis, amplification products are correlated with their presence in the mutant phenotypes and their absence in the wildtype phenotypes to identify the amplification product associated with the mutant phenotype. The particular genetic sequence of the amplification product(s) cosegregating with the phenotype of interest, which represents a portion of the gene or genetic regulatory region that was tagged with a transposable element, can then be isolated. For example, banding patterns detected on an electrophoretic gel can be correlated with mutant and wildtype phenotypes to accomplish cosegregation analysis. The particular band or bands cosegregating with the phenotype of interest, each of which represent a portion of the gene that was tagged with a transposable element, can then be excised from the gel and cloned. Methods for cloning the isolated amplification products are well known in the art. See particularly, Sambrook et al. (1989) *Molecular Cloning: A Laboratory Manual* (Cold Spring Harbor Laboratory, Plainview N.Y.), herein incorporated by reference.

In another exemplary method, bulk segregant analysis can be employed to identify the amplification product comprising the genetic sequence associated with the mutant phenotype. Michelmore et al., *Proc. Natl. Acad. Sci USA* 88:9828–9832 (1991); Pineda el al., *Genome* 36:152–156 (1992). In this method, DNA from homozygous wild-type organisms are combined and DNA from homozygous mutants are combined. Amplification products that are unique to the mutant group comprise the genetic sequence associated with the mutant phenotype. In some embodiments, the amplification product comprising the genetic sequence of interest can be obtained by subtractive hybridization of the collection of wild-type amplification products from the mutant collection of amplification products. In other embodiments, the amplification product comprising the genetic sequence of interest can be identified by screening each collection with probes for the adapter or transposable element and identifying the amplification product which is unique to the mutant collection.

The genetic sequence associated with the mutant phenotype may be used as a probe for southern blots, for cDNA library screening, or may be sequenced and compared to the databases for homology. Primers can be designed from the sequence gained from this method, and reverse genetics via TUSC (Benson el al. (1995) *Plant Cell* 7:75–84; Mena et al. (1996) *Science* 274:1537–1540; U.S. patent application Ser. No. 08/835,638, which is a continuation of U.S. patent application Ser. No. 08/262,056), as demonstrated in the examples, can confirm the cloned gene is responsible for the phenotype detected.

The transposable element amplification-based strategy of the present invention provides for the immediate molecular analysis of a transposable element-tagged gene of interest by allowing for direct isolation of DNA fragments comprising a genetic sequence, which is a portion of the transposable element-tagged gene/regulatory region. The combination of a preliminary fragmentation, a transposable element-directed amplification, and detection of the amplification products by such exemplary methods as high-resolution acrylamide gel electrophoresis produces small DNA fragments that extend directly from the inserted transposable element. Amplification products of interest can be isolated and used as probes or directly sequenced, thus eliminating the time-consuming steps of construction of a sub-genomic library, restriction mapping, and subcloning that are presently used in isolation and identification of transposon-tagged genes.

A modification of this approach provides a method for the identification of the location of an additional type of insertion event into genomic DNA, more specifically transgene insertion into the genome of a host organism, preferably a plant. In this embodiment of the invention, AFLP technology is paired with a transgene-anchored amplification to amplify genomic DNA fragments flanked by at least a portion of the transgene of interest and a known adapter sequence.

In this method, DNA is isolated from a transgenic organism comprising a transgene of interest whose DNA sequence is sufficiently well known to design a transgene specific primer which selectively hybridizes, under stringent conditions, to the transgene. Fragmentation and adapter attachment are performed as previously described. The resulting adapter-modified DNA fragments are then subjected to an amplification step using an adapter-derived primer and a primer derived from the DNA sequence for the transgene of interest. In this case, genomic DNA fragments comprising the flanking transgene will be amplified. As in the method for isolating a transposable element-tagged gene, this method may further comprise a preliminary PCR amplification that uses an adapter-derived primer paired with a transgene-derived primer. This preliminary PCR amplification may use primers with similar high Tm requirements (AFLP-like PCR) or with asymmetric Tm requirements (TAIL-PCR), as previously described.

Following detection of the amplification products, the amplification products can then be sequenced and/or used to probe mapping populations to determine the genomic location of each transgene insertion event.

The following examples are offered by way of illustration and not by way of limitation.

EXPERIMENTAL

The method of the present invention was used to isolate and identify the DNA sequence of the novel gene known as the lazy la1 gene of maize. The "lazy plant" phenotype results from a recessive mutation first observed in 1923 and later described by Jenkins and Gerhardt in 1931 (*Agric. Expt. Station, Iowa Slate Coll. Agric. Mech. Arts*, pp. 124–151). The la1 locus was mapped to chromosome 4, near tassel seed 5 (ts5), using morphological mutants (Emerson et al 1935).

Since that time, lay has been shown to lie between ts5 and floury 2 on the short arm of chromosome 4 (*Maize Genetics Cooperation Newsletter* 69 (1995):250). The nucleotide sequence for this gene is disclosed in copending application filed on Feb. 18, 1999 (U.S. Ser. No. 60/075,057) and entitled "*Compositions and Methods for Modification of the Gravitropic Response of Plants.*" This novel gene encodes a mutant protein whose function confers a prostrate growth habit to this mutant phenotype. Thus the growth habit of the developing and mature stem of the lazy plant exhibits positive gravitropism, or a so-called positive gravitropic response. By "positive gravitropic response" is intended growth toward gravity. Thus in the lazy plant, stem growth is the opposite gravitropic response as is generally found in nature. Growth of the root system of the lazy plant phenotype appears to be unaffected by this recessive mutation, hence the roots exhibit normal positive gravitropism.

Example 1

Source of Plant Material

A controlled cross pollination between the non-Mutator maize hybrid K61Pr (female) and an unnamed maize Mutator donor line (male) resulted in an F:1 ear. This ear was shelled and planted. One plant from this row was fertilized by controlled self pollination resulting in an F:2 ear. This F:2 ear was shelled and planted. These progeny were found to be segregating for the lazy (la1) mutation.

Example 2

Cloning of the Lazy Gene

Isolation of DNA

Ninety-nine individuals from a Mu-containing family segregating (78:21) for the lazy la1 gene (la1-63342) were phenotypically scored and DNA samples were isolated from leaf tissues. DNA preparation was carried out in 96-well plates by a proprietary method as described in the specifications for U.S. patent application Ser. No. 08/262,056 (Briggs et al., filed Jun. 17, 1994). However, use of a standard CTAB DNA preparation (Saghai Maroof et al. (1984) *Proc. Natl. Acad. Sci. USA* 81:8014–8019) would have provided suitable DNA as well.

General PCR Protocol

Isolated DNA samples from these individuals were first digested with a single restriction enzyme. Restriction digest was carried out with 50–500 ng DNA, 5 units concentrated restriction enzyme, 8.0 $\mu$l 5× restriction/ligation (RL) buffer (50 mM Tris.Hac at pH 7.5, 50 mM MgAc, 250 mM Kac, and 250 ng/$\mu$l BSA), and 0.2 $\mu$l 1.0 M DTT, diluted with water to a 40-$\mu$l final reaction volume, and incubated at 37° C. for 1 hr.

Adapter sequences were then ligated onto the restriction sites of the resulting restriction DNA fragments of each sample. Each restriction digest sample was spun down; 10 $\mu$l ligation mix (1.0 unit T4 DNA ligase (Pharmacia), 0.05 $\mu$l 1.0M DTT, 2.00 $\mu$l 5× RL buffer, 1.00 $\mu$l 10.0 mM ATP, and 50 pmoles of each adapter strand, diluted with water to the final reaction volume of 10.0 $\mu$l) was added directly to the digest; and each resulting sample was incubated at 37° C. for at least 4 hr, preferably overnight. Each restriction/ligation sample was then spun down, and a 10.0 $\mu$l aliquot removed and diluted with 90.0 $\mu$water (or TE).

The resulting adapter-modified DNA fragment samples were then subjected to the method of the present invention to isolate and identify the DNA sequence for this transposable element-tagged gene.

The preliminary round of amplification may entail an AFLP-like PCR or a TAIL-PCR, depending upon the desired level of preferential amplification of Mu-containing restriction DNA fragments, with the greatest preferential amplification being achieved with a TAIL-PCR.

When a standard AFLP-like PCR was used during the preliminary round of amplification, the following cycling profile was used: 95° C. for 1 min; then 94° C. for 1 min, 62° C. for 30 sec, and 72° C. for 2 min, repeated for a total of 19 cycles; followed by 94° C. for 1 min, 62° C. for 30 sec, 72° C. for 5 min, and held at 4° C. until further analysis.

When a TAIL-PCR method was used for generating preliminary PCR products, the following cycling profile was used: 95° C. for 1 min; then 94° C. for 1 min, 64° C. for 30 sec, and 72° C. for 2 min, repeated for a total of 5 cycles; then 94° C. for 1 min, 40° C. for 3 min, and ramping to 72° C. over 3 min; 94° C. for 1 min, 64° C. for 30 sec, 72° C. for 2 min, then 94° C. for 1 min, 64° C. for 30 sec, 72° C. for 2 min, 94° C. for 1 min, 42° C. for 30 sec, and 72° C. for 2 min, repeated for a total of 15 cycles; followed by 94° C. for 1 min, 42° C. for 30 sec, 72° C. for 5 min, and held at 4° C. until further analysis.

Regardless of the cycling profile, the PCR mix consisted of 5.0 µl adapter-ligated DNA fragment sample (0.6 ng DNA/µl), 1.5 µl transposon-derived primer (50 ng/µl), 1.5 µl adapter-derived primer (50 ng/µl), 5.0 µl PCR buffer (10×; 100 mM Tris (pH 8.3), 500 mM KCl, 20 mM $MgCl_2$, 30% DMSO), 1.0 µl dNTP (10 mM), and 0.2 units Taq Polymerase, with water added to make a final volume of 50.0 µl. These amplification products were quality checked by visualizing 10 µl of product on an EtBr-stained gel. The remaining products were diluted 10- to 100-fold (depending on the efficiency of the amplification) with water and served as template for subsequent PCR reactions.

The diluted products of the preliminary PCR were used as template for the secondary amplification, in which the Mu-TIR-derived primer was labeled thereby allowing detection of only the Mu-containing DNA fragments. Prior to PCR amplification, Mu-TIR-derived primer was labeled with $^{33}P$ by mixing 5.0 µl Pharmacia 10× buffer, 2.1 µl Pharmacia T4 kinase (9.5 units/µl), 22.9 µl $dH_2O$, 10.0 µl Mu-TIR-derived primer, and 10.0 µl $^{33}P$ ATP, and allowing the reaction to proceed at 37° C. for 30 min. The reaction was then terminated by incubating at 70° C. for 10 min. The resulting labeled Mu-ITR-derived primer mix #1 was then immediately added to 200.0 µl Boehringer-Mannheim 10× PCR buffer, 8.0 µl Boehringer-Mannheim Taq DNA polymerase (5 units/µl, added immediately prior to the addition of the labeled Mu-TIR derived primer mix #1), and 542.0 µl $dH_2O$. These components were mixed thoroughly and spun down to produce labeled Mu-TIR-derived primer master mix #2. An adapter-derived primer master mix #3 was also prepared, consisting of 60.0 µl adapter-derived primer (50 ng/µl), 80.0 µl dNTPs (5 mM), and 560.0 µl $dH_2O$. The resulting volumes of these mixes allow for running 100 samples, each of which includes 0.50 µl labeled primer mix #1.

The secondary PCR amplification was then run using the diluted products of the primary PCR as template DNA and mixes #2–3 as follows. In brief, 5.0 µl of each template DNA sample and 7.0 µl of adapter-derived master mix #3 were added to a reaction vessel and stored on ice (if necessary) until addition of 8.0 µl of labeled Mu-TIR primer master mix #2, yielding a final reaction volume of 20 µl.

Because there are many different adapter-derived primer possibilities (depending on the restriction enzymes used in the initial digestion of the DNA), a "touchdown" PCR strategy was employed. In brief, the initial programmed annealing temperature of the cycling profile was 2° C. higher than the Tm of the Mu-TIR-derived primer. In each of the next 7 cycles, the programmed annealing temperature was reduced by 1° C. For the next 25 cycles, the programmed annealing temperature remained at ((Tm Mu-TIR primer +2)−7). Thus, for example, if the Tm of the Mu-TIR-derived primer is 64° C., the cycling profile for the secondary PCR would be as follows: 95° C. for 1 min; then 94° C. for 1 min, 64° C. for 30 sec, 72° C. for 2 min, 94° C. for 1 min, 63° C. for 30 sec, 72° C. for 2 min, 94° C. for 1 min, 62° C. for 30 sec, 72° C. for 2 min, 94° C. for 1 min, 61° C. for 30 sec, 72° C. for 2 min, 94° C. for 1 min, 60° C. for 30 sec, 72° C. for 2 min, 94° C. for 1 min, 59° C. 30 sec, 72° C. for 2 min, 94° C. for 1 min, 58° C. for 30 sec, 72° C. for 2 min, 94° C. for 1 min, 57° C. for 30 sec, and 72° C. for 2 min; followed by 94° C. for 1 min, 57° C. for 30 sec, and 72° C. for 2 min, repeated for a total of 25 cycles; and then 94° C. for 1 min, 57° C. for 30 sec, 72° C. for 2 min, and held at 4° C. until further analysis.

Specific Digestion and PCR Protocol for Isolation of Lazy Gene

A restriction digest was performed with the four-base-pair cutting restriction enzyme MseI, generating restriction DNA fragments with overhang restriction sites.

Adapter sequences specific for the MseI-derived overhang restriction sites were ligated to the restriction sites of the DNA restriction fragments.

These adapter-ligated DNA fragments were then subjected to a preliminary PCR amplification using a high-TM Mu-TIR-derived primer and a high-TM adapter-derived primer and following the standard AFLP-like PCR protocol described above, comprising 20 thermocycles. The amplification products of the preliminary PCR were diluted 10-fold, and the resulting dilutions were used for a secondary PCR amplification using a touchdown of annealing temperatures with labeled Mu-derived primer. This amplification step used a nested $^{33}P$ labeled Mu-TIR derived primer and a nested adapter-derived primer and followed a touchdown PCR cycling profile similar to that described above. The touchdown PCR had an initial annealing temperature of 63° C. reduced to a final annealing temperature of 56° C. over 7 cycles. An additional 25 cycles were performed at the 56° C. annealing temperature.

Detection of the labeled PCR products of this second PCR was accomplished using acrylamide gel electrophoresis and autoradiography. A band was found to cosegregate with the lazy phenotype. This 320 bp fragment was excised from the gel and cloned. Sequencing of the cloned la1-63342 amplicon revealed a 241 bp fragment after the Mu-TIR and adapter sequences were trimmed.

This cosegregating PCR product was also verified using fluorescent-based technology. First, a preliminary TAIL-PCR according to the protocol described above was employed using the MseI digested, adapter/ligated DNA as template. A high-Tm Mu-TIR-derived primer was paired with a low-Tm adapter-derived primer. The amplification products from this original reaction were diluted 100-fold and used as template for a secondary touchdown PCR with an initial annealing temperature of 63° C. reduced to a final annealing temperature of 56° C. over 7 cycles. An additional 25 cycles were performed at the 56° C. annealing temperature. The Mu-TIR-derived primer was labeled with TET. Product separation and detection was performed on the ABI 377 Prism instrument according to the manufacturer's protocols and conditions. Primer labeling was also performed according to ABI protocols.

Screening the Pioneer EST database resulted in only two clones with significant homology to the la1-63342 amplicon. CIMAJ89R5 is derived from a shoot culture cDNA library, while CBHGG34R5 comes from a hypomethylated genomic library. An intron splice site is recognizable in the CIMA sequence at position 100, and only 189 bp of sequence was available. CBHGG34R5 and amplicon la1-63342 share nearly 100% identity excepting the intron region. These two clones were retrieved from archives for further characterization, and after full insert sequencing was done, comparison to the public databases was performed. No sequences in the public databases share significant homology to the lazy clones.

Initially, only 20 of each phenotypic class were screened. An additional mutant and 25 additional wildtypes were screened using a dot-blot approach. DNAs from these 66 individuals were cut with MseI, adapters were ligated, and cold Mu-selective amplification was used to generate PCR products. These products were applied to a Zetaprobe nylon membrane via a Bio-Rad 96-well vacuum blotter. All of the mutants hybridized with the cDNA CIMAJ89R5, and 31 of the phenotypically wildtypes hybridized with the probe. The original Mu-containing la1-63342 amplicon was used as a probe and produced an identical hybridization pattern as the EST clone.

Mapping of Lazy Clones

In order to confirm linkage of our clones to the classically mapped la1 locus, CBHGG34R5 was used as a probe to screen an F2 mapping population consisting of 100 individuals. cDNA CIMAJ89R5 was hybridized to the Southerns to insure the two clones would give identical banding patterns and were of the same copy number in the genome. The two RFLP markers that were found to flank CBHGG34R5 also flank the la1 locus. Taken together, the mapping data and the cosegregation data provide exceptional confidence that the la1-63342 Mu-containing amplicon, and the clones CIMAJ89R5 and CBHGG34R5, were in fact representative of the la1 locus. This confidence led to the designing of a primer to be used in the reverse genetics screen of TUSC (Bensen et al. (1995) *Plant Cell* 7:75–84; Mena et al. (1996) *Science* 274:1537–1540; U.S. patent application Ser. No. 08/835,638, which is a continuation of U.S. patent application Ser. No. 08/262,056) to find additional mutant alleles of la1.

TUSC

Pairing a la1-63342 amplicon-derived primer with a Mu-TIR-derived primer, TUSC identified another unique lay allele. The Mu-containing la1*-231 amplicon was cloned and sequenced to confirm identity. This insertion is nearly 600 bp downstream from the la1-63342 insertion. Twenty-five individuals from the F2 family (PV03 116 D-8) derived from this TUSC pool were planted in the nursery and did indeed segregate (14:6) for the lazy phenotype.

These segregating individuals were leaf-sampled and DNA was isolated. Southern blots of these samples were probed with the cDNA CIMAJ89R5 to confirm cosegregation with the lazy phenotype. All lazy individuals contain only one band (homozygous mutant allele), which hybridizes to the CIMA clone. The wild-type individuals show banding patterns of either a single non-mutant band (homozygous wt), or both bands (heterozygous). PCR analysis was used to confirm the presence of Mutator in all of the mutants.

Expression

Northern data suggests that the lazy transcript is found in several tissues, but not in roots, and that CIMAJ89R5 represents the full length message. In situ hybridization was carried out using RNA probe derived from the full length lazy cDNA. The vegetative apex of the seedling was surrounded by about 5 leaves resulting from expansion of preformed embryonic leaf primordia. Lazy signal was visible in the center of the coleoptilar node, about 300 $\mu$m below the apex. At this level, the coleoptile connects with the oldest leaf and the mesocotyl. The lazy signal does not coincide with vascular bundles, rather the cells between.

While no significant homology has been found to any other previously characterized nucleic acid sequence, some weak homology at the amino acid level is found between the putative lazy peptide and Sec Y protein. While the amino acid homology is only conserved 100 residues, by comparing secondary structure predictions the similarity is enhanced, and similarity of structure extends nearly 200 residues.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for the identification and isolation of a genetic sequence from an organism, wherein disruption of genomic DNA of said organism by a transposable element flanking said genetic sequence is associated with a mutant phenotype, said method comprising the following steps:
    a) segregating a plurality of organisms by the presence or absence of said mutant phenotype, wherein the genomic DNA of each organism comprises at least one copy of said transposable element;
    b) obtaining a mutant genomic DNA sample from at least one of said organisms exhibiting said mutant phenotype and a wild-type genomic DNA sample from at least one of said organisms not exhibiting said mutant phenotype;
    c) fragmenting at least one of said mutant and at least one of said wild-type genomic DNA samples to produce DNA fragments;
    d) attaching an adapter to at least one of said mutant DNA fragments and to at least one of said wild-type DNA fragments, resulting in a collection of adapter-modified DNA fragments;
    e) amplifying said mutant and wild-type adapter-modified DNA fragments to yield amplification products comprising said genetic sequence wherein said amplification employs a first oligonucleotide primer which selectively hybridizes under stringent hybridization conditions to said adapter sequence, and a second oligonucleotide primer which selectively hybridizes under stringent hybridization conditions to said transposable element; and,
    f) isolating an amplification product present in said organism exhibiting said mutant phenotype and absent in said organism not exhibiting said mutant phenotype, wherein said isolated amplification product comprises said genetic sequence associated with said mutant phenotype.

2. The method of claim 1, wherein step (f) comprises using cosegregation analysis to isolate said amplification product that cosegregates with said mutant phenotype.

3. The method of claim 1, wherein step (f) comprises using bulked segregant analysis to isolate said amplification product.

4. The method of claim 1, wherein said transposable element is a transposable element that comprises a terminal inverted repeat (TIR) sequence.

5. The method of claim 4, wherein said transposable element is a member of the Mutator family of transposable elements.

6. The method of claim 5, wherein Mutator-TIR is a template for said second oligonucleotide primer.

7. The method of claim 1, wherein said organisms are plants.

8. The method of claim 7, wherein said plant is a maize plant.

9. The method of claim 1, further comprising a second amplification to preferentially amplify adapter-modified DNA fragments, wherein said second amplification employs at least two oligonucleotide primers, with one of said primers selectively hybridizing under stringent hybridization conditions to said adapter sequence, and the other primer selectively hybridizing, under stringent hybridization conditions, to said transposable element.

10. The method of claim 9, wherein said primers of said second amplification are nested within said primers of step (e) of claim 1.

11. The method of claim 1, wherein said amplification of step (e) is achieved by polymerase chain reaction (PCR).

12. The method of claim 1, wherein said fragmentation of step (c) is achieved by digestion with at least one restriction enzyme.

13. The method of claim 1, wherein said mutant genomic DNA sample of step (b) comprises genomic DNA from at least 2 organisms and said wild-type genomic DNA sample comprises genomic DNA of 10 organisms.

14. The method of claim 1, wherein at least one of said oligonucleotide primers is labeled.

15. A method for identifying one or more locations of a genomic Insertion by a transgene in genomic DNA of an organism, said method comprising the following steps:

a) isolating a genomic DNA sample from said organism;

b) fragmenting said isolated genomic DNA sample to yield a collection of DNA fragments;

c) attaching an adapter sequence to at least one of said DNA fragments to yield a collection of adapter-modified DNA fragments;

d) amplifying said adapter-modified DNA fragments, wherein said amplification employs a first primer which selectively hybridizes under stringent hybridization conditions to said adapter sequence, and a second primer which selectively hybridizes under stringent hybridization conditions to said transgene sequence; and e) analyzing said amplification products to identify the location of said genomic insertion.

16. The method of claim 15, wherein said organism is a plant.

17. The method of claim 15, further comprising a second amplification to preferentially amplify adapter-modified DNA fragments, wherein said second amplification employs at least two oligonucleotide primers, with one of said primers selectively hybridizing under stringent hybridization conditions to said adapter sequence and the other primer selectively hybridizing under stringent hybridization conditions to said transgene.

18. The method of claim 16, wherein said transgenic organism is a maize plant.

19. The method of claim 17, wherein said primers are nested with the primers of claim 15.

20. The method of claim 15, wherein said amplification is achieved by polymerase chain reaction (PCR).

21. The method of claim 15, wherein the fragmentation of step (b) is achieved by digestion with at least one restriction enzyme.

* * * * *